(12) United States Patent
Henshaw et al.

(10) Patent No.: US 8,720,251 B2
(45) Date of Patent: May 13, 2014

(54) GAS SENSING SYSTEM

(75) Inventors: Geoffrey Stephen Henshaw, Auckland (NZ); John Wagner, Auckland (NZ); Simon Naisbitt, Auckland (NZ); Bryon Wright, Auckland (NZ)

(73) Assignee: Aeroqual Limited, Auckland (NZ)

( * ) Notice: Subject to any disclaimer, the term of this patent is extended or adjusted under 35 U.S.C. 154(b) by 148 days.

(21) Appl. No.: 13/206,882

(22) Filed: Aug. 10, 2011

(65) Prior Publication Data

US 2012/0036916 A1 Feb. 16, 2012

(51) Int. Cl.
*G01N 27/02* (2006.01)

(52) U.S. Cl.
USPC ........................................................ 73/23.21

(58) Field of Classification Search
USPC ........................................................ 73/23.21
See application file for complete search history.

(56) References Cited

U.S. PATENT DOCUMENTS

| | | | |
|---|---|---|---|
| 3,652,227 A * | 3/1972 | Harman et al. | 436/118 |
| 6,993,955 B1 | 2/2006 | King et al. | |
| 7,140,232 B2 | 11/2006 | Wright et al. | |
| 2007/0215469 A1* | 9/2007 | Imamura | 204/424 |
| 2007/0245803 A1* | 10/2007 | Tan et al. | 73/31.05 |
| 2007/0269346 A1 | 11/2007 | Wohltjen | |
| 2009/0040044 A1* | 2/2009 | Chiao et al. | 340/540 |

OTHER PUBLICATIONS

Williams et al., "Development of Low-Cost Ozone and Nitrogen Dioxide Measurement Instruments Suitable for Use in an Air Quality Monitoring Method", May 2009, ECS Transactions, vol. 19, No. 6, p. 251-254.*

Schmidt, R.W.H., et al., "A selective ozone scrubber for application in ambient nitrogen dioxide measurements using the commercial luminox (LMA-3, Scintrex/Unisearch Inc.)", Atmospheric Environment, 29(8):947-950 (1995).

Viricelle, J.P., et al., "Selectivity improvement of semi-conducting gas sensors by selective filter for atmospheric pollutants detection," Materials Science and Engineering C 26:186-195 (2006).

Helmig, D., "Ozone removal techniques in the sampling of atmospheric volatile organic trace gases," Atmospheric Environment, 31(21):3635-3651 (1997).

Dhandapani, B., et al., "Gas phase ozone decomposition catalysts," Applied Catalysis B: Environmental 11:129-166 (1997).

* cited by examiner

*Primary Examiner* — Peter Macchiarolo
*Assistant Examiner* — Irving A Campbell
(74) *Attorney, Agent, or Firm* — James Creighton Wray

(57) ABSTRACT

A gas detection system comprising a gas sensor having a detection surface for detecting an analyte gas, the accuracy of detection being degraded by the presence of an unwanted gas at the sensor, and a thermal scrubber layer directly adjacent said detection surface of the gas sensor defining a diffusion path for the analyte and unwanted gases to traverse through to the detection surface, the diffusion path having a sufficient length and the thermal scrubber being heated by the heater to a sufficient temperature capable of at least partially thermally decomposing the unwanted gas prior to contacting the detection surface to thereby improve the accuracy of the sensor. The system further comprises a heater that is preferably arranged to heat both the detection surface and the thermal scrubber. The invention is particularly useful for improving the performance of an $NO_2$ gas sensor in the presence of ozone ($O_3$).

16 Claims, 4 Drawing Sheets

GAS SENSING SYSTEM

FIELD OF THE INVENTION

The invention relates to a gas sensing device or system comprising a thermal scrubber associated with the gas sensing device.

BACKGROUND OF THE INVENTION

Gas sensors or gas detectors are devices that determine the presence and/or measure the concentration of a target gas. Many sensors, such as metal oxide gas sensors based on Tin ($SnO_3$), Indium ($In_2O_3$) or Tungsten ($WO_3$) for example, exhibit good sensitivity to some gases such as nitrogen dioxide ($NO_2$). Typically, these sensors also exhibit high sensitivity to ozone ($O_3$). This makes them difficult to use as gas detectors/sensors in ambient air measurements due to the presence of $O_3$.

Systems for limiting sensor exposure to ozone are known. Such systems may utilise an ozone scrubber in front of the gas sensor to limit the exposure of the device to ozone. The ozone scrubber for example may use chemicals that react with ozone to convert it into another substance less affective to the sensor, or use a catalyst that converts ozone into oxygen. Such scrubbers however tend to produce reaction products that may be corrosive to the sensor material and/or affect the operability of the sensor.

It is an object of the present invention to provide an improved system and method for mitigating the effects of unwanted gas on a gas sensor and/or to at least provide the public with a useful choice.

SUMMARY OF THE INVENTION

In a first aspect the invention may broadly be said to consist of a gas detection system comprising:
 a gas sensor having a detection surface for detecting an analyte gas, the accuracy of detection being degraded by the presence of an unwanted gas at the sensor,
 a heater, and
 a thermal scrubber layer directly adjacent said detection surface of the gas sensor and defining a diffusion path for the analyte and unwanted gases to traverse through to the detection surface, the diffusion path having a sufficient length and the thermal scrubber being heated by the heater to a sufficient temperature capable of at least partially thermally decomposing the unwanted gas prior to contacting the detection surface to thereby improve the accuracy of the sensor.

Preferably the thermal scrubber layer is formed from an inert material.

Preferably in diffusion path length is in the range of 0.05 to 5 mm.

Preferably the thermal scrubber layer is a plate mounted parallel to and spaced from the detection surface to form a cavity therebetween and adjacent the detection surface for the analyte gas to diffuse into via the diffusion path defined by the ceramic plate. The plate may be a ceramic, glass or metal plate. The plate may be mounted on the gas sensor via a ceramic adhesive.

Preferably the ceramic plate comprises one or more perforations through the plate that define the diffusion path for gas. More preferably the plate comprises one or more apertures formed through the plate and perpendicular to the detection surface. Preferably the tile is of a 2×2×0.25 mm size and has twenty five apertures of 100 µm diameter formed through the plate and arranged in a 5×5 array. Alternatively the tile has a single aperture traversing through a centre of the plate.

Alternatively the diffusion path is defined by one or more channels formed between the plate and the gas sensor and traversing from outside the plate to the cavity.

Preferably the gas sensor is a sensor plate having a semiconducting metal oxide detection layer deposited on the detection surface of the plate, the detection layer changing electrical resistance with presence and/or change in concentration of the target gas.

Preferably the plate has deposited on the detection surface tracks for electrical current to flow through.

Preferably the system further comprises a body for holding the sensor and for retaining electrodes connected to said tracks for providing a means to deliver electrical current to the tracks from a power source and for providing the necessary connection for measuring an electrical resistance of the detection layer.

Preferably the plate has deposited on an opposing surface to said detection surface one or more heating tracks for heating up the sensor plate.

Preferably the heating tracks are heated by the heater and the scrubber layer is heated by contact with the plate.

Preferably the thermal scrubber layer is an alumina tile. Preferably the tile is the same length and width as the sensor plate.

The target gas may be any combination of nitrogen oxide ($NO_x$), e.g. nitrogen dioxide ($NO_2$) or nitric oxide (NO), carbon monoxide (CO), hydrogen sulfide ($H_2S$), ammonia ($NH_3$), sulfur dioxide ($SO_2$), and/or aromatic hydrocarbons and is preferably $NO_2$. The unwanted gas may be ozone ($O_3$).

In a second aspect the invention may broadly be said to consist of gas sensor having a heated zone directly adjacent a gas detection surface of the gas sensor, said heated zone defining a diffusion path to the gas sensor of sufficient length and temperature for at least partially decomposing an unwanted gas traversing through the diffusion path prior to contact with the detection surface to thereby improve accuracy of the gas sensor.

In a third aspect the invention may broadly be said to consist of a thermal scrubber of inert material for use in a gas detection system having a gas sensor and a heater, the thermal scrubber adapted to be heated by the heater and closely coupled to the gas sensor and is perforated to define a gas diffusion path of sufficient length and temperature to at least partially thermally decompose an unwanted gas diffusing through the scrubber to the sensor.

In a fourth aspect the invention may broadly be said to consist of a method of accurately detecting the presence of an analyte gas in the presence of an unwanted gas, said method comprising:
 providing an analyte gas sensing means, and
 forming a hot zone directly adjacent the gas sensing means for gas to diffuse through to the gas sensing means, the hot zone defining a diffusion path of sufficient length and temperature to at least partially decompose the unwanted gas prior to contact with the gas sensing means.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

Figure 1:
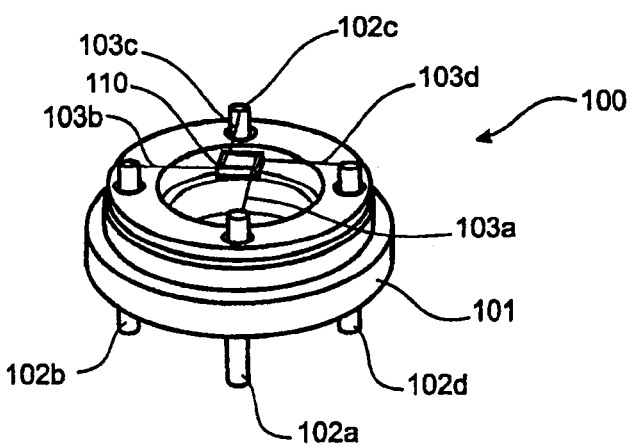
FIG. 1 is a perspective view of a preferred form gas sensing system of the invention.

Referring to FIG. 1 a preferred form of gas sensor 100 is shown having a main structural body component 101 that provides sensor 100 handling capability for the user and holds/retains a sensor plate 110 and electrodes 102a-d electrically coupled to the sensor plate 110 for providing electrical potential to the plate 110 and for measuring electrical current flowing through the plate 110. The sensor plate 110 is shown suspended above the main body 101 via electrically conductive lines 103a-d. The electrodes are shown retained through respective apertures of the body 101.

The body 101 can be made from any suitable non-conductive material such as a plastics material and may be formed to any suitable shape and size for the particular application. The body 101 as stated above provides the sensor 100 with structure and is not intended to be an essential feature of the invention as it does not affect the operation that will be discussed in more detail below. Similarly any number and type of electrodes 102a-d may be employed as required by the application but generally four will provide the necessary electrical connection points for a typical gas detector. Typically, two of the electrodes will connect to an electrical power supply to provide an electrical potential across the sensor plate 110 for current to flow through the plate, and two other electrodes are provided to connect a current sensing device or similar to the plate to measure an output current or resistance indicative of the type and/or concentration of analyte gas or gases contacting the plate.

Figure 2:
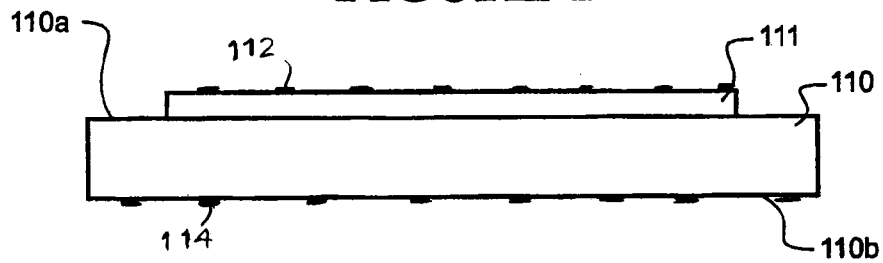
FIG. 2 is a cross-sectional view from the side of a preferred form sensor plate of the invention.

Referring now to FIG. 2, the sensor plate 110 has a layer 111 of semiconducting gas detecting material deposited on surface 110a of the plate 110. In the preferred embodiment layer 111 is a metal oxide layer 111. Interdigitated electrically conductive tracks 112 are formed/deposited on the same surface 110a to connect the semiconducting metal oxide layer 111 to the electrodes 102a-d (via lines 103a-d). In an alternative embodiment, lines 103a-d are not provided and the tracks are connected directly to electrodes or connection points. In the preferred embodiment, the surface 110b (opposite surface 110a having the interdigitated tracks and metal oxide layer 111) has heating tracks 114 formed/deposited thereon. These tracks are preferably platinum heating tracks but may be formed from any other suitable heat conductive material.

The sensor plate 110 in operation has its heating tracks connected to a heating element (hereinafter referred to as heater) to heat up the plate 110 and in particular the metal oxide layer 111. The heated semiconducting metal oxide layer 111 will undergo a change in electrical resistance when a specific gas or when certain gases contact the layer 111 and/or when the concentration of an analyte gas changes, causing the current flowing through the interdigitated tracks to be altered thereby providing a means for identifying or indicating the concentration of an analyte gas.

Any suitable material may be deposited on the surface 110a of plate 110 for detection of gas provided the material observes an electrical property that changes in accordance with the type and/or concentration of the analyte gas as required by the particular application. Furthermore, the material may be heated to any temperature that will enable it to operate as described above. The temperature can be maintained at a constant temperature T, or can have a varying profile if required by the application.

The metal oxide layer 111 deposited on the sensor plate 110 may for example enable detection/measurement of the concentration of any one or more of the following gases: any form of nitrogen oxide ($NO_x$), e.g. nitrogen dioxide($NO_2$) or nitric oxide (NO), carbon monoxide (CO), hydrogen sulfide ($H_2S$), ammonia ($NH_3$), sulfur dioxide ($SO_2$), and/or aromatic hydrocarbons.

In the preferred embodiment, the metal oxide layer 111 is a tungsten based ($WO_3$) layer heated to approximately 300° C. during operation. The WO, layer of the preferred embodiment is particularly useful for the detection of presence of nitrogen dioxide ($NO_2$) gas in the vicinity of the sensor 100. $WO_3$ exhibits good sensitivity to $NO_2$. However, the $WO_3$ layer also exhibits a high sensitivity to ozone ($O_3$). In ambient air measurements, the presence of ozone therefore degrades the performance of the sensor 100 in detecting an analyte gas such as $NO_2$ as the $WO_3$ detection layer 111 changes resistance in the presence of both $NO_2$ and ozone.

Figure 3:
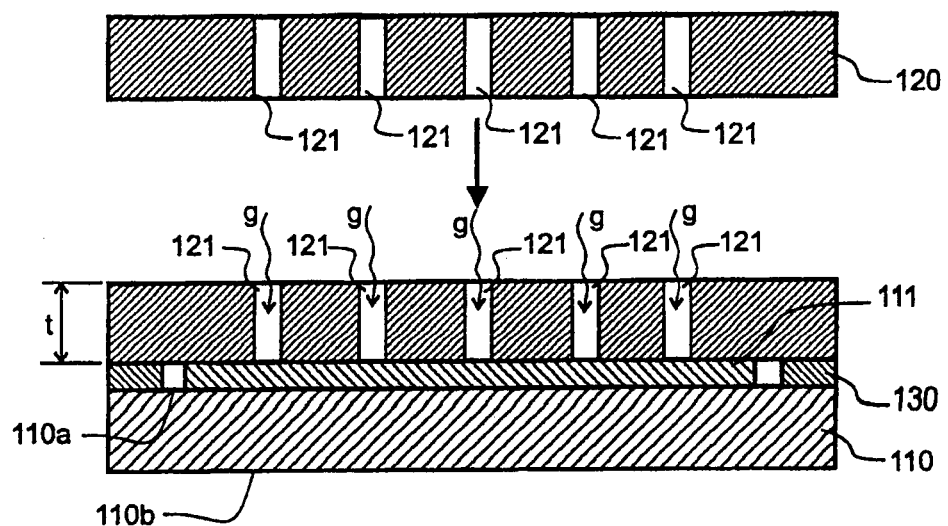
FIG. 3 is a cross-sectional view from the side of a preferred form thermal scrubber of the invention shown separate from and couple to the sensor plate of FIG. 2.

Referring now to FIG. 3, ozone sensitivity is significantly reduced by using an integrated thermal scrubber layer 120. The integrated thermal scrubber in the preferred form is an inert plate or tile over layer 120 mounted on top of the surface 110a of the plate 110. In the preferred embodiment the tile 120 is made from alumina. The alumina tile 120 is perforated (including microperforated) to allow gases to diffuse through to the sensor plate surface 110a and in particular to the $WO_3$ detection layer 111 as shown by arrows g. In the embodiment of FIG. 3, the tile 120 is shown having apertures 121 for diffusion of gas g. The apertures are perpendicular to the surface 110a and layer 111 of the sensor plate 110. The scrubber may less preferably be a porous over layer.

The tile 120 in FIG. 3 is shown mounted on top of surface 110a of sensor plate 110 using a ceramic adhesive 130. Any other suitable adhesive can be used to mount the tile 120 to the surface 110a of plate 110. Preferably however the adhesive is thermally conductive. Alternatively the tile may be mechanically mounted. In one preferred embodiment (not shown by FIG. 3), the tile 120 may be mounted parallel to and spaced from the detection layer 111 to thereby form a cavity between the detection layer 111 and the tile 120 for the analyte gas to sit in after diffusing through the thermal scrubber 120. This enhances performance as the gas is allowed to settle in an area adjacent the detection layer 111.

In operation, the tile 120 is heated due to thermal contact with sensor plate 110. In an alternative embodiment the tile 120 is not in contact with the sensor plate 110 and/or detection layer 111 and is mounted above the sensor plate 110 and heated by a separate heater for example. In the preferred embodiment, power consumption is reduced through the use of a single heater to heat up the sensor plate 110 and the tile 120. As gases g (composed of ozone and $NO_2$ for instance) approach the sensor 100 they are heated by the tile 120 and diffuse through the apertures 121 to the detection layer 111. Above a certain temperature, ozone becomes thermally unstable and decomposes. As ozone diffuses through the tile, it will heat up and decompose before reaching the detection layer 111. The analyte gas ($NO_2$ in the preferred embodiment) however, is not as unstable as ozone at such temperatures and therefore diffuses through the apertures 121 of tile 120 to the $W_3$ detection layer 111 without decomposing to the same extent as ozone. The use of an integrated thermal scrubber 120 thus makes it possible to measure the presence and/or concentration of $NO_2$ more accurately and selectively in the presence of ozone in the environment.

Furthermore, the thermal scrubber 120 defines a diffusion path for the analyte gas to the detection layer 111. The scrubber 120 also heats the analyte gas prior to contact with the detection layer 111 which can improve performance. The scrubber 120 can be of any shape and allows gas diffusion in any manner provided it is closely associated with the detection layer 111 of the sensor 100 and it is heated to the appropriate temperature for decomposing gas that affects operation of the sensor 100 (such as ozone). In effect, the scrubber 120 provides a hot zone above the detection layer 111 for gas to diffuse through prior to contact with the detection layer. The thermal scrubber 120 is closely coupled to the sensor plate 110 and is a layer of material not significantly larger than the sensor plate 110. Thus it can be heated with minimal power consumption and preferably by the same heater as that used for heating the plate 110.

The thermal scrubber 120 is also designed to have a time-temperature profile for decomposing the unwanted gas to a predetermined extent. The diffusion path has a sufficient length, and the thermal scrubber is heated by the heater to a temperature, to at least partially thermally decompose the unwanted gas prior to contact with the detection layer to thereby improve the accuracy of the sensor. For the embodiment of FIG. 3 this suggests a minimum thickness t of the tile 120 is associated with the temperature of the tile 120 for achieving the required level of decomposition. It is a preferred embodiment of the invention that the length of the diffusion path defined by the thermal scrubber 120 is in the range of 0.05-5 mm.

Figure 4:
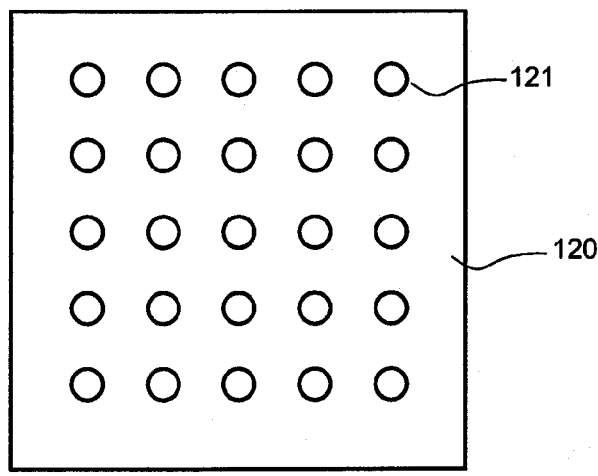
FIG. 4 is a plan view of the thermal scrubber of FIG. 3.

FIG. 4 shows an exemplary embodiment of a thermal scrubber 120 design of FIG. 3 in plan, The alumina tile 120 may be a 2 mm×2 mm plate with a thickness t (as shown in FIG. 3) of 0.25 mm. The tile 120 comprises 25 holes 121 of 0.1 mm diameter arranged in a 5×5 array. The holes are evenly spaced such that the distance between the centres of two holes is 0.333 mm as shown. The holes 121 may for example be laser ablated through the tile 120. The associated sensor plate 110 can also be a 2 mm×2 mm plate 110 with a $WO_3$ detection layer 111 heated at 300° C. The tile 120 can be mounted above the sensor plate 110 using a ceramic adhesive. The resulting sensor 100 provides a higher $NO_2/O_3$ sensitivity ratio than an equivalent metal oxide gas sensor without tile 120. The thickness t of the tile 120 in this instance is sufficient to decompose enough ozone at 300° C. to enable operability of the gas sensor 100 for detection of $NO_2$ gas to the required level of accuracy.

The analyte gas is not limited to $NO_2$ and the thermal scrubber 120 is not limited to a design suitable for decomposing ozone. The invention may be used to decompose or at least partially decompose any unwanted gas diffusing through the thermal scrubber with the analyte gas if such unwanted gas affects the performance of the sensor 100 in accurately detecting and/or measuring the concentration of the analyte gas.

There can be any number of suitable apertures 121 through the tile 120. Furthermore, grooves or channels running through from the side of the tile 120 may be present to allow diffusion of gas from the side the tile 120. For example, one or more channels may be formed between the tile 120 and the sensor plate 110 for gas to diffuse through and into a cavity formed between the tile 120 and the detection layer 111. The thermal scrubber 120 is also not necessarily planar and other geometries which control gas diffusion to the sensor detection layer 111 are also intended to be included within the scope of the invention. The scrubber 120 can be made of any suitable material that is thermally stable and rigid, such as metal, ceramics or glass. The scrubber 120 can be screen printed or layered above the sensor plate 110 through chemical vapour deposition (CVD) or physical vapour deposition (PVD) for example. The apertures 121 can be formed in any suitable manner. For instance they can be machined through an impermeable scrubber layer of inert ceramic via a laser or other device (as described in the example above) or they may be integrally formed in a microporous gas permeable scrubber layer. The thermal scrubber layer may further comprise a catalyst or other chemical to chemically decompose the unwanted gas or ozone in conjunction with thermal decomposition. The above variations are not intended to be excluded from the scope of the invention.

Figure 5:
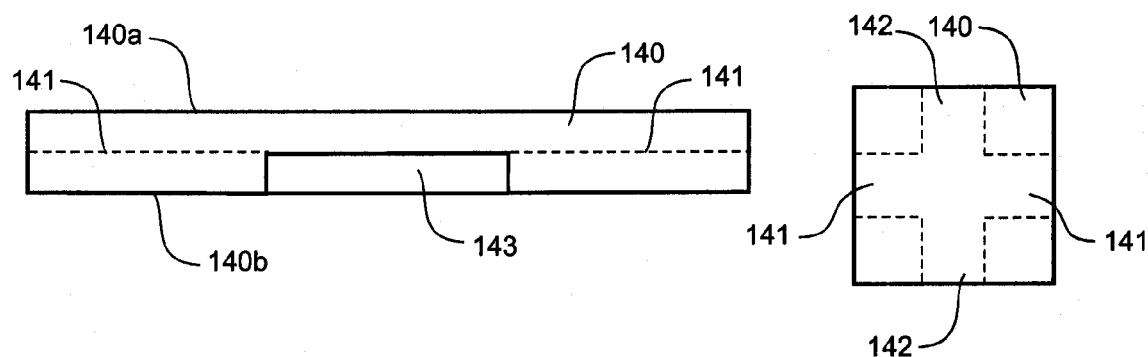
FIG. 5 is cross-sectional views from the top and side of a second thermal scrubber embodiment.
Figure 6:
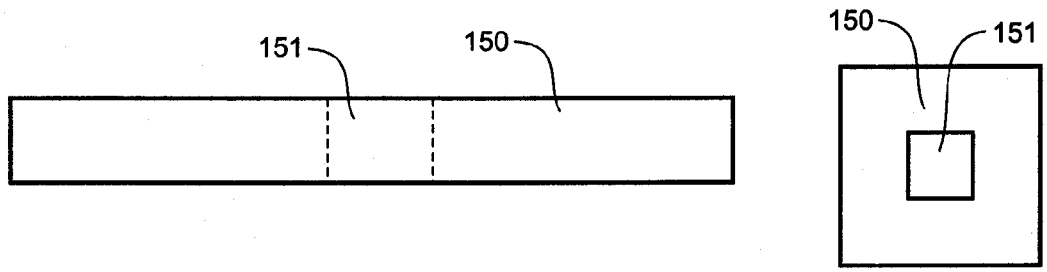
FIG. 6 is cross-sectional views from the top and side of a third thermal scrubber embodiment.

FIGS. 5 and 6 show alternative thermal scrubber designs 140 and 150 respectively. In FIG. 5 the tile 140 is shown to have side and end channels 141 and 142 respectively extending to a central cavity 143 at the underside 140b of the tile 140 to the midsection of the tile 140. In this embodiment it is not required to have apertures or holes through the entire tile with the side and end channels 141 and 142 leading to cavity 143 and providing a sufficient diffusion path for the gases. FIG. 6 shows a tile 150 with a single central aperture 151 through the tile 150 which may be sufficient for decomposing any unwanted gas to the required level in some applications.

Experiment

Figure 7:
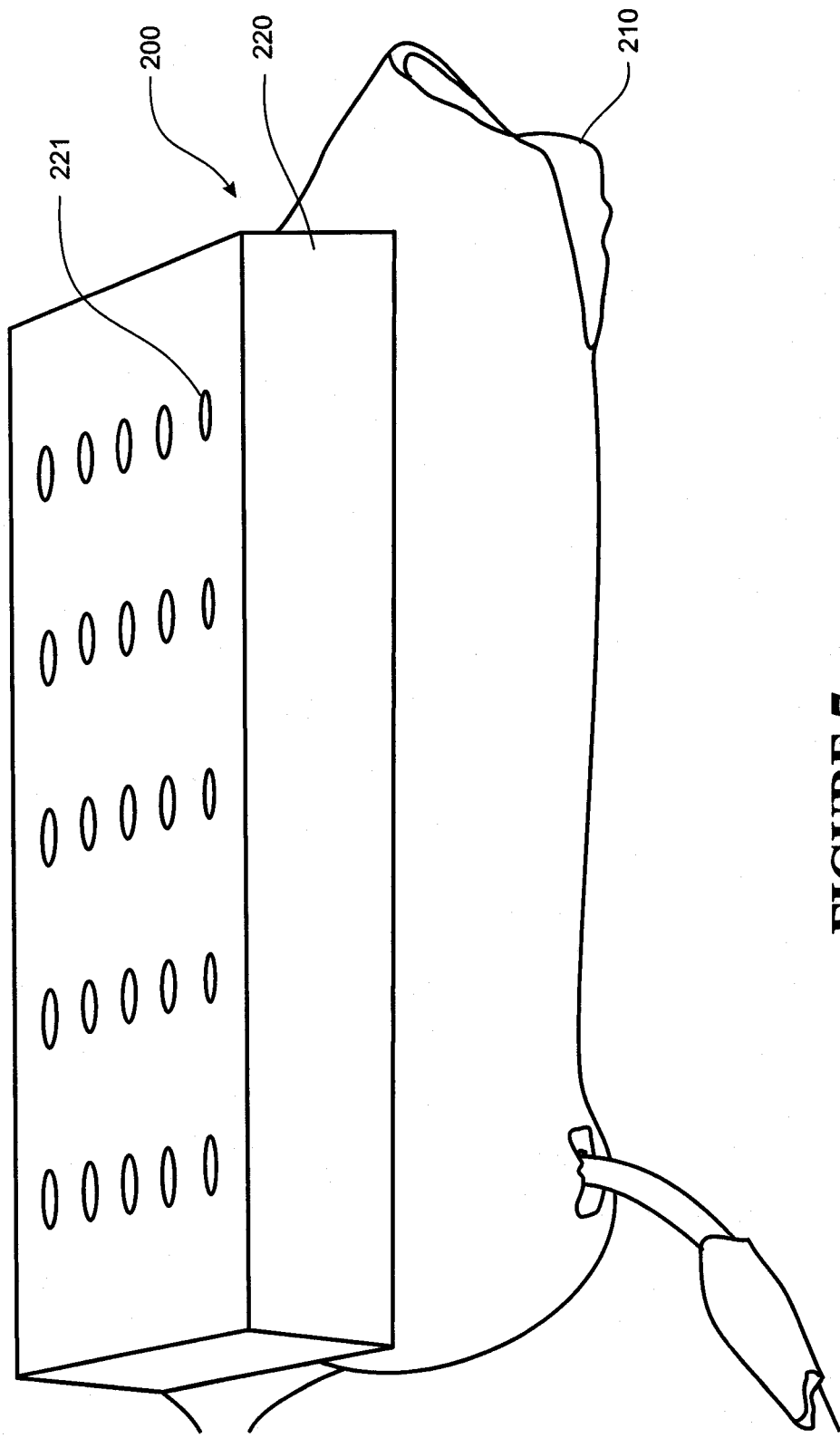
FIG. 7 is a perspective view of a practical form gas sensing system of the invention used in an experiment.
Figure 8:
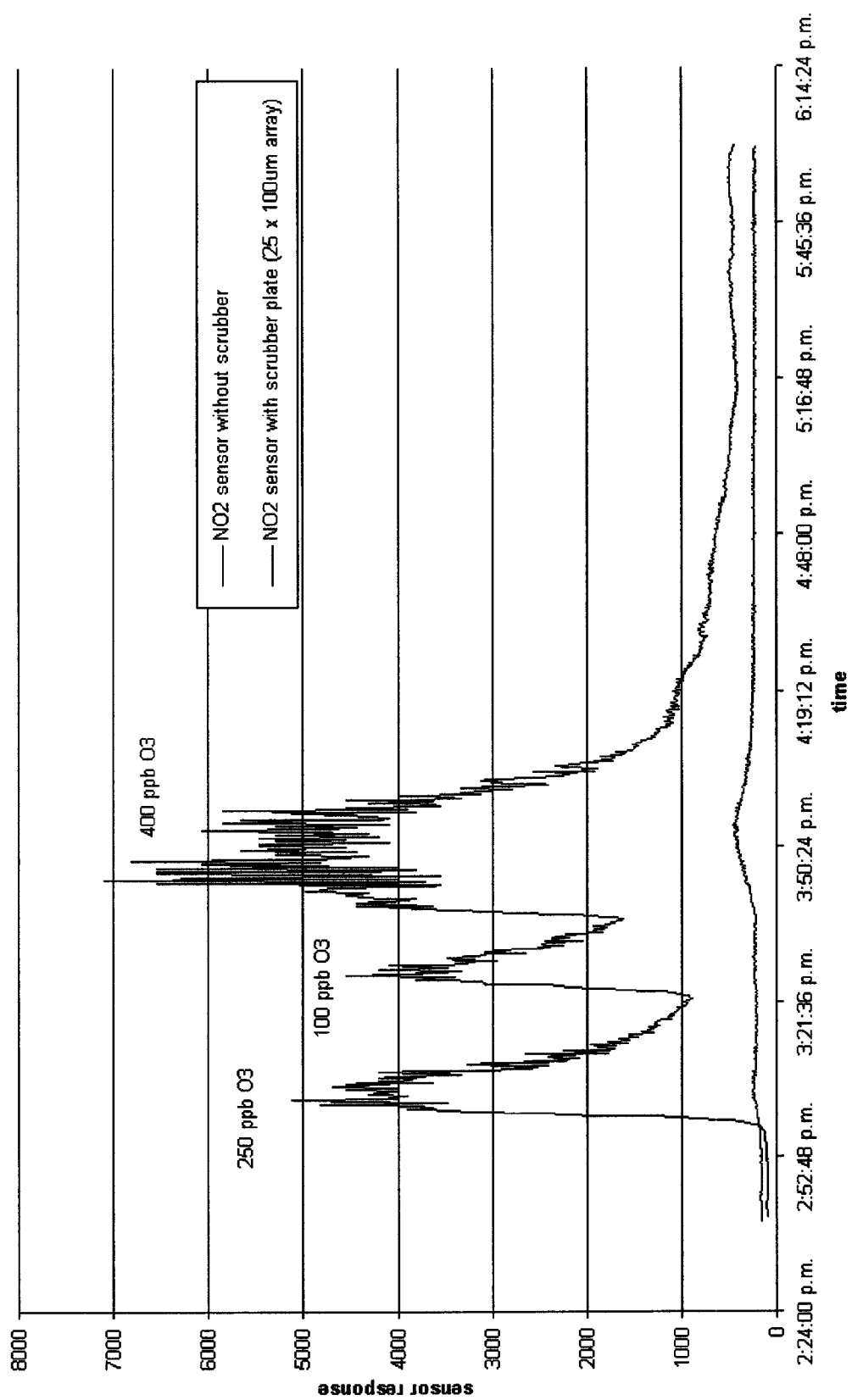
FIG. 8 is a graph showing the sensitivity of a gas sensing system to ozone with the thermal scrubber vs. the sensitivity of a gas sensing system to ozone without the thermal scrubber.

Referring now to FIGS. 7 and 8, an $NO_2$ sensor 200 was fabricated from a 2 mm×2 mm×0.25 mm alumina tile with a platinum (Pt) heater track on one side and gold inter-digitated electrodes on the other (not shown). $WO_3$ was screen printed on top of the gold electrodes to form a detection layer. An alumina tile 220 of the same dimensions as the sensor tile/detection layer was modified by laser cutting a 5×5 array of 100 micron diameter holes 221 through it to form a thermal scrubber tile 220. This scrubber tile 220 was bonded on top of the $WO_3$ sensor layer using a ceramic dielectric adhesive. The sensor was heated via a current through the Pt heater and the resistance of the $WO_3$ layer measured via the gold electrodes.

The resistance of the platinum tracks was measured in a chamber into which a known concentration of $O_3$ in air mixture was introduced. FIG. 8 shows a graph of the response of the sensor 200 with different concentrations of $O_3$ being introduced. The response of a similar sensor without the scrubber tile 220 was also measured and plotted. The response of both sensors to $NO_2$ was substantially the same, however, the resistance change to $O_3$ of the sensor 200 with the scrubber tile 220 was found to be significantly reduced compared to a sensor without the scrubber tile. This is shown in FIG. 8, where the resistance of the tracks in the sensor without the scrubber were largely altered by the introduction of $O_3$ at various different concentrations. The resistance of the sensor 200 with the scrubber tile 220 remained substantially constant as $O_3$ was introduced.

This experiment demonstrated that $O_3$ would not interfere (at least to the same extent as a conventional $NO_2$ sensor) in an $NO_2$ measurement in ambient air using a sensor 200 with the scrubber tile 220.

The foregoing description of the invention includes preferred forms thereof. Modifications may be made thereto without departing from the scope of the invention as defined by the accompanying claims.

The invention claimed is:

1. A gas detection system comprising:
a gas sensor having a detection surface for detecting an analyte gas, the accuracy of detection being degraded by the presence of an unwanted gas at the sensor,
a heater, and
a thermal scrubber layer contiguous to said detection surface of the gas sensor and defining a diffusion path for the analyte and unwanted gases to traverse through to the detection surface, the diffusion path having a sufficient length and the thermal scrubber being heated by the heater to a sufficient temperature capable of at least partially thermally decomposing the unwanted gas prior to contacting the detection surface to thereby improve the accuracy of the sensor.

2. A gas detection system according to claim 1 wherein the diffusion path length is in the range of 0.01 to 5 mm.

3. A gas detection system according to claim 1 wherein the thermal scrubber layer is formed from an inert material.

4. A gas detection system according to claim 1 wherein the thermal scrubber layer is a scrubber plate mounted contiguous to the detection surface and having a diffusion path traversing therethrough to the detection surface.

5. A gas detection system according to claim 4 wherein the scrubber plate comprises one or more perforations through the scrubber plate that define the diffusion path for gas.

6. A gas detection system according to claim 4 wherein the scrubber plate is 2 mm wide by 2 mm long by 0.25 mm deep, and comprises a 5×5 array of 100 μm diameter apertures traversing along the depth of the plate for defining the diffusion path.

7. A gas detection system according to claim 4, wherein the gas sensor further comprises a sensor plate having the detection surface, and wherein the scrubber plate is mounted on the sensor plate parallel to and spaced from the detection surface to form a cavity therebetween and adjacent the detection surface for the analyte gas to diffuse into the cavity via the diffusion path of the plate.

8. A gas detection system according to claim 7 wherein the scrubber plate comprises one or more channels formed between the scrubber plate and the gas sensor and traversing from outside the scrubber plate to the cavity to define the diffusion path for gas.

9. A gas detection system according to claim 4 wherein the scrubber plate is a ceramic plate, a metal plate or a glass plate.

10. A gas detection system according to claim 1 wherein the gas sensor further comprises a sensor plate, and further comprising a semiconducting metal oxide detection layer deposited on the detection surface of the sensor plate, the detection layer changing electrical resistance with presence or change in concentration of the target gas or both.

11. A gas detection system according to claim 10 wherein the sensor plate has deposited on the detection surface tracks for electrical current to flow through.

12. A gas detection system according to claim 11 wherein the heater further comprises one or more heating tracks deposited on an opposing surface of the sensor plate to said detection surface tracks, wherein the heating tracks heat the sensor plate, and thus heat the scrubber layer through thermal contact of the scrubber layer with the sensor plate.

13. A gas detection system according to claim 11 further comprising a body for holding the sensor and for retaining electrodes connected to the tracks for providing electrical current to the tracks from a power source and for measuring an electrical resistance of the detection layer.

14. A gas detection system according to claim 1 wherein the gas sensor has a detection surface for detecting the presence or concentration or both of any one or combination of nitrogen oxide ($NO_x$), e.g. nitrogen dioxide ($NO_2$) or nitric oxide (NO), carbon monoxide (CO), hydrogen sulfide ($H_2S$), ammonia ($NH_3$), sulfur dioxide ($SO_2$), ozone ($O_3$), volatile organic compounds, and/or aromatic hydrocarbons and wherein the accuracy of the detection is degraded by the presence of ozone ($O_3$) or volatile organic compounds at the detection surface.

15. Apparatus comprising a thermal scrubber of inert material for use in a gas detection system having a gas sensor and a heater, the thermal scrubber comprising a diffusion path configured to be heated by the heater and the diffusion path being closely coupled contiguous to the gas sensor, the diffusion path being of sufficient length and temperature to at least partially thermally decompose an unwanted gas diffusing through the scrubber to the sensor.

16. A method of detecting an analyte gas in the presence of an unwanted gas, said method comprising:
providing an analyte gas sensor, and
forming a heated scrubber zone contiguous to the gas sensor for gas to diffuse through to the gas sensor, the heated scrubber zone defining a diffusion path of sufficient length and temperature to at least partially decompose the unwanted gas prior to contact with the gas sensor.

* * * * *